(12) United States Patent
Sadhu

(10) Patent No.: US 8,247,547 B2
(45) Date of Patent: Aug. 21, 2012

(54) **PROCESS FOR THE PREPARATION OF *CARALLUMA* EXTRACT AND A FORMULATION PREPARED THEREOF**

(76) Inventor: Ghare Vishwas Sadhu, Thane (IN)

( * ) Notice: Subject to any disclaimer, the term of this patent is extended or adjusted under 35 U.S.C. 154(b) by 272 days.

(21) Appl. No.: 12/696,815

(22) Filed: Jan. 29, 2010

(65) Prior Publication Data

US 2010/0197617 A1  Aug. 5, 2010

(30) Foreign Application Priority Data

Jan. 30, 2009 (IN) .......................... 185/MUM/2009

(51) Int. Cl.
*C07H 1/06* (2006.01)
*C07H 1/08* (2006.01)
*A01N 45/00* (2006.01)

(52) U.S. Cl. ..................................... 536/128

(58) Field of Classification Search .................. None
See application file for complete search history.

(56) References Cited

U.S. PATENT DOCUMENTS 7,060,308 B2  6/2006  Rajendran
7,390,516 B2  6/2008  Rajendran

*Primary Examiner* — Layla Bland
(74) *Attorney, Agent, or Firm* — Robert P. Michal; Lucas & Mercanti, LLP

(57) ABSTRACT

Processes for the preparation of *Caralluma* extract which includes shade-drying of *Caralluma* plant material; ii) treating the dried *Caralluma* plant material by at least one operation selected from a group consisting of sorting, cleaning and sizing to obtain *Caralluma* plant material meant for extraction or any combination thereof; iii) extracting the *Caralluma* plant material with a first solvent for at least two initial iterations followed by at least two subsequent iterations with a second solvent at controlled temperature to obtain a diluted extract; iv) removing the solvent from the diluted extract by distillation at a temperature below about 40° C. to obtain a concentrate; v) chilling the concentrate at a temperature of about 6 to about 10° C. for a period of about 7 to about 8 hours to obtain a chilled concentrate; vi) filtering the chilled concentrate to obtain a filtrate; vii) concentrating the filtrate at a temperature below about 60° C. to obtain a viscous liquid; viii) spray-drying the concentrated viscous liquid to obtain a powder; and ix) pulverizing and sifting the dried powder to obtain a *Caralluma* extract provided. Such extracts may be included in medicinal formulations used for the prevention and treatment of obesity and obesity-related conditions for subjects in need thereof.

5 Claims, 1 Drawing Sheet

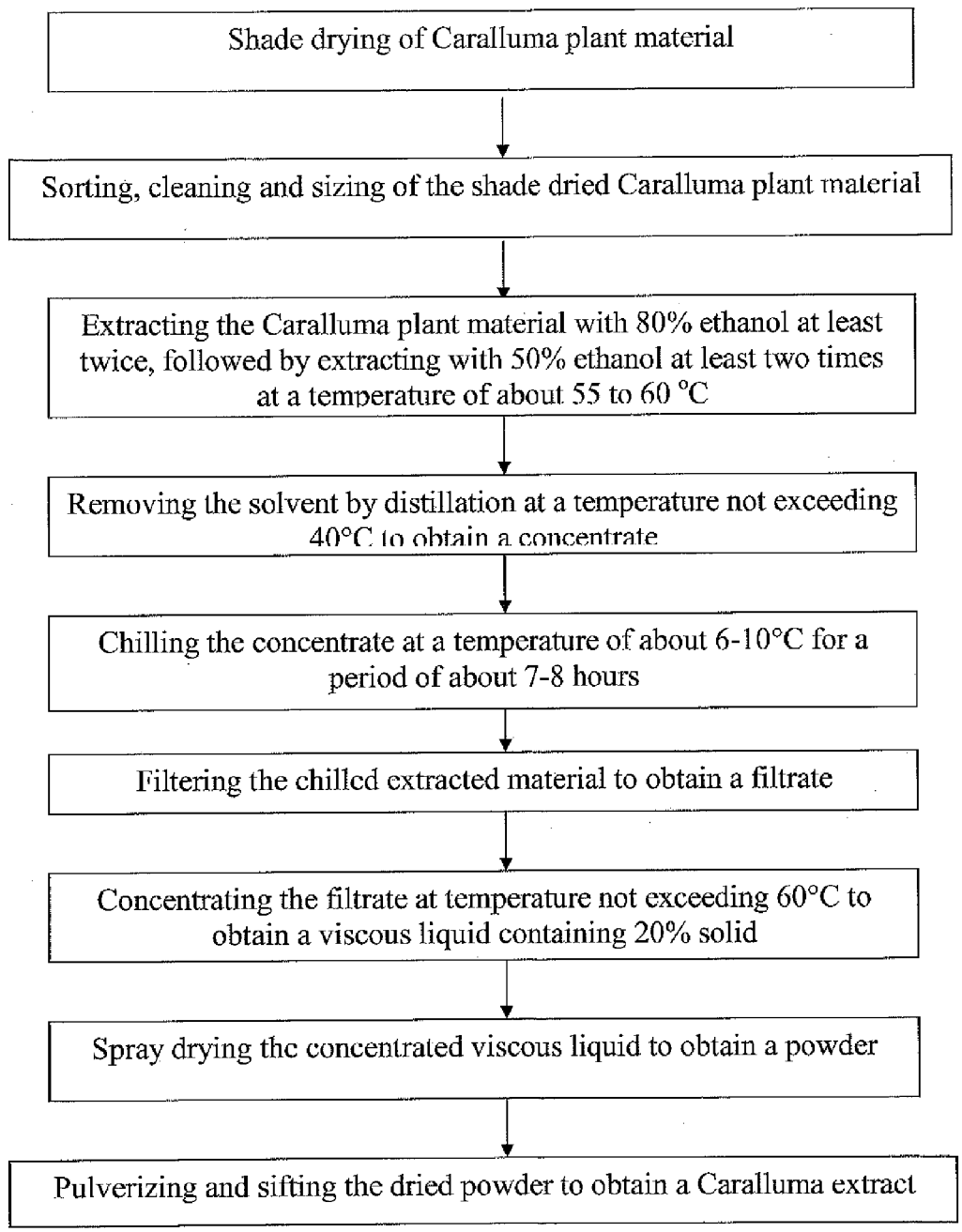

PROCESS FOR THE PREPARATION OF *CARALLUMA* EXTRACT AND A FORMULATION PREPARED THEREOF

RELATED APPLICATION

This application claims priority to and benefit of Indian Application No. 185/MUM/2009 30-01-2009 IN filed on Jan. 30, 2009, the contents of which are hereby incorporated by reference in their entirety.

FIELD OF THE INVENTION

The present invention relates to plant extracts. In particular, the invention relates to a process for extracting essential constituents from plants and formulations prepared therefrom.

BACKGROUND OF THE INVENTION

The *Caralluma* genus belongs to the plant family Asclepiadaceae. The genus *Caralluma* includes of a number of plant species such as *Caralluma burchardii, Caralluma acutangula, Caralluma adscendens, Caralluma edulis, Caralluma fimbriata, Caralluma negevensis, Caralluma somalica, Caralluma speciosa* etc. *Caralluma* plants have been reported to possess medicinal properties such as anti-diabetic, anti-inflammatory, antiobesity etc. which have been attributed to its chemical constituents, particularly glycosides belonging to the pregnane group. A glycoside is a condensation product obtained from a sugar and non-sugar compound and may have further components like ring structures that are substituted or non-substituted.

*Caralluma fimbriata*, also known as "famine food" in India, is a succulent plant, found as a roadside shrub or boundary marker. It has been eaten in rural India for centuries in raw form, as a vegetable with spices, or preserved in chutneys and pickles. It has been used as a portable food and thirst quencher for hunting. It has also been used for its purported ability to suppress hunger and appetite and enhance stamina.

*Caralluma fimbriata* is believed to block the activity of several enzymes, which then block the formation of fat, forcing fat reserves to be burned. *Caralluma fimbriata* is also believed to have an effect on the appetite control mechanism of the brain. It has been shown to be effective in reducing body fat through appetite control. In addition, the extract of this plant is widely recommended for diabetics due to its hypoglycemic activity.

In a study conducted on *Caralluma fimbriata*, fifty overweight individuals were given either a placebo or one gram of extract each day for sixty days resulting in significant reduction in appetite and waist circumference of the non-control group.

Key phytochemical constituents of the herb are pregnane glycosides, flavone glycosides, megastigmane glycosides and saponins. The pregnane glycosides act as an inhibitor in the process of adipocyte cell division. These glycosides significantly inhibit adipogenesis and therefore can contribute to the management of obesity and regulation of body parameters and related disorders.

Obesity is a major health problem occurring all over the world. In majority of cases, certain lifestyle factors are major contributors of obesity. These lifestyle factors reinforce the genetic pre-disposition towards obesity leading to its exacerbation. Such lifestyle factors include: sedentary lifestyle, high calorie food, high fat and salt consumption, processed food consumption, psychological factors etc. Obesity is also a major factor for various other diseases like diabetes, cardiovascular diseases, including hypertension etc.

A number of references describe certain methods for obtaining and extracting *Caralluma* extract.

For example, U.S. Pat. No. 7,060,308 describes a *Caralluma* extract and a method of making same, which can be standardized and is reproducible. Such methods are said to prevent the glycosides from decomposing, which can reduce undesirable non-glycoside components. As described, in a first *Caralluma* extract, the resinous material does not exceed 0.5% by weight, and, in the second *Caralluma* extract, the resinous material does not exceed 1.0% by weight. The first extract is produced by optional pretreatment of plant materials, optional crushing and/or grinding, extraction, and concentration. The filtration step and the resin removal step also may be performed optionally. Hexane is used to remove the gums and resins in this reference. The second extract is produced by contacting the first *Caralluma* extract with excipients, drying, powdering, sifting and blending.

Likewise, U.S. Pat. No. 7,390,516 describes a similar method of making *Caralluma* extract which can be standardized and is reproducible. This reference also states that the method disclosed therein prevents the glycosides from decomposing, which can reduce the undesirable non-glycoside components. Removal of gums and resins is also carried out with of hexane.

The methods of extraction described in these and other references have several common problems which include: (1) The disclosed methods are time-consuming and/or (2) The disclosed methods use hexane to remove the gums and resins in order to prevent charring of the product during concentration. Unfortunately hexane is known to be carcinogenic and may prove to be harmful andor (3) Some references describe the use of certain drying aids like malto dextrin or magnesium carbonate which interfere with the quality of the final product and adds to the cost of production as well.

SUMMARY OF THE INVENTION

A primary object of the present invention is to provide an improved process for the preparation of *Caralluma* extract.

Another object of the present invention is to provide an improved process which avoids the use of carcinogenic solvents such as hexane.

Still another object of the present invention is to provide an improved process which is simple to perform and is less time-consuming.

A further object of the present invention is to provide an improved process which provides pure and high yield of essential constituents from the plant for preparation of *Caralluma* extract.

A still further object of the present invention is to provide an improved extract having appetite-suppressing and weight-controlling activities.

Still another object of the present invention is to provide formulations containing *Caralluma* extract.

Yet another object of the present invention is to provide methods of treating or preventing obesity and conditions associated with obesity by administering formulations containing *Caralluma* extract to subjects in need thereof.

In accordance with the present invention there is provided processes for making *Caralluma* extracts; said processes including the following steps:

a. Shade-drying *Caralluma* plant material;
b. treating the dried *Caralluma* plant material by at least one operation selected from a group consisting of sorting, cleaning and sizing to obtain *Caralluma* plant material meant for extraction or combinations thereof;

c. extracting the *Caralluma* plant material with a first solvent for at least two initial iterations followed by at least two subsequent iterations with a second solvent at controlled temperature to obtain a diluted extract;

d. removing the solvent from the diluted extract by distillation at a temperature below about 40° C. to obtain a concentrate;

e. chilling the concentrate at a temperature of about 6 to about 10° C. for a period of about 7 to about 8 hours to obtain a chilled concentrate;

f. filtering the chilled concentrate to obtain a filtrate;

g. concentrating the filtrate at a temperature below about 60° C. to obtain a viscous liquid containing about 20% solid;

h. spray drying the concentrated viscous liquid to obtain a powder; and i. pulverizing and sifting the dried powder to obtain a *Caralluma* extract.

*Caralluma* plant material may be obtained from the group of *Caralluma* species including *Caralluma burchardii*, *Caralluma acutangula*, *Caralluma adscendens*, *Caralluma edulis*, *Caralluma fimbriata*, *Caralluma negevensis*, *Caralluma somalica*, and *Caralluma speciosa*, or combinations thereof.

BRIEF DESCRIPTION OF DRAWINGS

FIG. 1 provides a flowchart of a representative process for the preparation of *Caralluma* extract in accordance with the present invention.

DETAILED DESCRIPTION OF THE INVENTION

The present invention provides, inter alia, improved processes for the preparation of *Caralluma* extract:

A representative process for a process according to the present invention is shown in FIG. 1. As shown therein, the first step may include shade drying of the plant material to obtain plant material in dry form. The next step may include treating the plant material in order to make it suitable for the extraction. In certain embodiment of the invention it may be desirable to reduce the size of the plant in order to make it suitable for the extraction process, since smaller sizes provide enhanced contact during the processing steps and consequently allow faster extraction process. The plant material may be sorted, cleaned and sized to reduce its size to obtain a plant material more suitable for extraction processes.

The *Caralluma* plant material may be extracted with a first solvent for at least two initial iterations followed by at least two subsequent iterations with a second solvent at controlled temperature to obtain a diluted extract. The next step may include removing the solvent from the diluted extract by distillation at a temperature below about 40° C. to obtain a concentrate. The obtained concentrate may then be chilled at a temperature of about 6 to about 10° C. for a period of about 7 to about 8 hours to obtain a chilled concentrate.

The chilled concentrate may be filtered to obtain a filtrate which is preferably free of gums and resinous material and concentrated at a temperature below about 60° C. to obtain a viscous liquid containing about 20% solid. In certain embodiments the viscous material may be about 10% solid and in other embodiments about 30% solid. Ranges between about 10 and about 30% or less than 10% or more than 30% may be obtained in some embodiments. The viscous liquid may be further spray-dried in order to obtain a powder. Finally the powder may be pulverized and sifted to obtain a *Caralluma* extract.

The *Caralluma* plant material used in accordance with the present invention may be obtained from the group of *Caralluma* species consisting of *Caralluma burchardii*, *Caralluma acutangula*, *Caralluma adscendens*, *Caralluma edulis*, *Caralluma fimbriata*, *Caralluma negevensis*, *Caralluma somalica*, and *Caralluma speciosa* or any combination thereof.

In certain embodiments the *Caralluma* plant material is preferably *Caralluma fimbriata*.

In accordance with the present invention the first and second solvent used for extracting the *Caralluma* plant material may be selected from a group consisting of water, methanol, ethanol, isopropyl alcohol, n-butanol and hydro alcohol and combinations thereof.

In certain embodiments, the first and second solvent used for extracting the *Caralluma* plant material is preferably ethanol.

In accordance with certain embodiments the present invention the concentration of the first solvent used for extraction may be about 80%. In other embodiments, concentrations of the first solvent may be higher or lower than 80%.

In accordance with certain embodiments the present invention the concentration of the second solvent used for extraction may be about 50%. In certain embodiments, concentrations of the second solvent may be higher or lower than 50%.

In accordance with certain embodiments the present invention the step of extraction may be carried out at a temperature in the range of about 55 to about 60° C.

In another embodiment of the present invention there is provided a *Caralluma* extract characterized by presence of about 30 to about 35% of pregnane glycosides; about 10 to about 15% of saponin glycosides; and about 0.20 to about 0.80% of resinous material.

Embodiments of the present invention also include medicinal formulations which contain *Caralluma* extract obtained as described herein. Such medicinal formulations generally include:

a. *Caralluma* extract in an amount of about 20 to about 80% mass of the formulation; and b. pharmaceutically acceptable excipients Medicinal formulations according to the present invention may include caralluma extract formulated as a powder, liquid, tablet, pill, capsule, suspension, emulsion, injectable and the like.

Pharmaceutically acceptable excipients which may be used to prepare a medicinal formulation in accordance with the present invention include binders, diluents, disintegrating agents, matrix forming agents, lubricants, glidents, coating agents, polymers, surfactants, preservatives, antioxidants, pH-adjusting agents and solvents.

Medicinal formulations according to the present invention may be administered to subjects in need thereof. Such formulations are affective in, for example, appetite suppression and weight reduction. Accordingly, the present invention also includes methods of treatment or prevention of obesity and conditions associated with obesity in subjects in need thereof.

When administered, extracts according to the present invention are believed to block the activity of several enzymes, which then block the formation of fat, forcing fat reserves to be burned. Extracts according to the present invention are also believed to have an effect on the appetite control mechanism of the brain thereby reducing body fat through appetite control. Such extracts also have a favorable effect on hypoglycemic activity in, for example, diabetic subjects.

The cell cycle is a complex process, wherein, during G1-S and G2-M of the cell cycle there is sequential activation of cyclin-dependent kinases (CDKs) in association with regulatory subunits namely cyclins. Without being bound by any particular theory, the inhibition mechanism for the 3T3-L I pre-adipocyte proliferation by *Caralluma* extracts (produced as described herein) during an early phase of adipogenesis may involve either down-regulation of CDK which plays role in facilitation the transcription of genes necessary for S-phase DNA synthesis or inhibition of import of cyclin D1-CDK bolo-enzyme from the cytosol into the nucleus. *Caralluma* extract is believed to induce G1 arrest in the pre-adipocyte cells through prevention of import of cyclin D1 into the nucleus.

Following examples illustrate certain aspects of embodiments of the present invention, but are not intended to limit its scope.

Example 1

Representative Process for the Preparation of *Caralluma* Extract

The stems of the plant *Caralluma* fimbriata were collected and dried in shade. The shade dried plant material was sorted, cleaned and sized by a crusher to obtain ready to extract material. About 100 gms of the *Caralluma* plant material was extracted with 300 ml of 80% ethanol twice. This was followed by washing the material with 300 ml of 50% ethanol four times, at controlled temperature 55 to 60° C. Then the solvent was removed by distillation at a temperature below 40° C. under vacuum to obtain a concentrate of 600 ml. The concentrate was then chilled at a temperature of about 8° C. for about 8 hours. The chilled extracted material thus obtained was filtered. The residue was discarded and filtrate was collected. The filtrate was then concentrated at a temperature below 60° C., under vacuum, to obtain a viscous liquid containing about 20% solid. The concentrated viscous liquid was spray-dried to obtain powder. The dried powder thus obtained was pulverized and sifted to obtain the desired *Caralluma* extract.

The *Caralluma* extract obtained from the aforesaid process was analyzed for the presence of various chemical constituents such as glycosides, resins and the like and compared with an extract obtained by the older, less effective process described in U.S. Pat. No. 7,060,308.

TABLE 1

Comparison of *Caralluma* Extract of prior art and present invention

| TEST PARAMETER | (U.S. Pat. No. 7,060,308) | Present Invention |
|---|---|---|
| Appearance | Brown to dark brown powder | Light Brown to Brown colored powder |
| Solubility in water | Soluble | Soluble |
| Total Bitters | 3% minimum w/w | 3.0% minimum w/w |
| Loss on drying | 10% maximum w/w | 8.0% maximum w/w |
| Total saponin glycosides | 10 to 30% w/w | 10.0% to 15.0% w/w |
| Total pregnane glycosides | Above 30% w/w | 30.0% to 35.0 5% w/w |
| Resinous matters | Not more than 1% w/w | Not more than 0.8% w/w |
| Total microbial count | 5000 cfu/gram max | 1000 cfu/gram |
| *E. coli* and *Salmonella* | Absent | Absent |
| Coliforms | Absent | Absent |

TABLE 1-continued

Comparison of *Caralluma* Extract of prior art and present invention

| TEST PARAMETER | (U.S. Pat. No. 7,060,308) | Present Invention |
|---|---|---|
| *P. aeruginosa* | Absent | Absent |
| *S. aureus* | Absent | Absent |
| Heavy metals | 10 ppm maximum | 10 ppm maximum |

Examples 2 and 3 below provide data from pre-clinical studies of *Caralluma fimbriata* (CF) extract obtained by processes described herein.

Example 2

Acute Oral Toxicity and Subchronic Toxicity Testing of *Caralluma Fimbriata* (CF) Extract in Rats Female Wistar albino rats (6 in number, aged between 8 to 12 weeks), were maintained in standard environmental conditions of temperature (25±2° C.). The animals were fed with standard diet, water and a specially prepared diet rich in fat. Artificial lighting was provided in the sequence of 12 hrs light and 12 hrs dark. Animals were housed individually.

Dose:

Dose progression was done in a sequence of 1.75, 5.5, 17.5, 55, 175, 550, 1750, 2000 and 5000. The *Caralluma* fimbriata (CF) extract test substance was formulated in a freshly prepared aqueous solution.

Administration of Test Substance:

Animals were fasted prior to dosing, their fasted body weight was noted and the dose was calculated according to the body weight. The test substance was administered in a single dose by oral gavage using a stomach tube on a fixed time between 9.00 am to 10.00 am. The observation of acute oral toxicity and subchronic toxicity testing of *Caralluma* Extract (CF) in rats is provided below.

(a): CNS and ANS Activity:

Sub-chronic toxicity study on wistar rats was done as per OECD guidelines, using a dose of 200 mg/kg body weight of CF extract of the present invention. The limit test and main test do not show any adverse effect on CNS and ANS activities. The CNS and ANS activities were normal throughout the study. (Table 2)

TABLE 2

Effect of *Caralluma* extract (CF) on ANS and ANS Activity

| S. NO. | SIGNS | REMARKS ON EFFECT |
|---|---|---|
| 1 | Tremors | x |
| 2 | Clonic Convulsions | x |
| 3 | Straub reaction | x |
| 4 | Pilo-erection | x |
| 5 | Muscle spasm | x |
| 6 | Catatonia | x |
| 7 | Spasticity | x |
| 8 | Loss of righting reflex | x |
| 9 | Sedation | x |
| 10 | Muscle relaxation | x |
| 11 | Anesthesia | x |
| 12 | Lacrimation | x |
| 13 | Diarrhea | x |
| 14 | Salivation | x |
| 15 | Writhing | x |
| 16 | Respiration a. Depression b. Stimulation | x |

TABLE 2-continued

Effect of *Caralluma* extract (CF) on ANS and ANS Activity

| S. NO. | SIGNS | REMARKS ON EFFECT |
|---|---|---|
| 17 | Skin color | x |
|  | a. Cyanosis |  |
| 18 | Vasodilatation | x |

(b): Biochemical Estimations (Liver and Kidney Function Analysis)

Sub-chronic toxicity study on Wistar rats was done as per OECD guidelines, using a dose of 200 mg/kg body weight of CF extract. CD (Cafeteria Diet) group showed significant increase in serum creatinine levels which were reversed in CD (Cafeteria Diet)+CF (*Caralluma* Extract) treated group. CD+CF extract treated group showed no significant rise in blood urea level when compared to control untreated group and CD group. There was slight rise in serum uric acid levels in CD+CF extract treated group. (Table 3)

TABLE NO. 3

Blood levels of Urea, Creatinine and Uric acid: (Kidney function tests)

| Groups | Blood Urea (mg/dl) | Creatinine (mg/dl) | Uric Acid (mg/dl) |
|---|---|---|---|
| Control Untreated N = 6 | 43.17 ± 4.79 | 0.600 ± 0.176 | 3.31 ± 0.68 |
| Cafeteria diet (C.D.) N = 6 | 39.33 ± 2.65 | 0.426 ± 0.06 | 1.63 ± 0.29 |
| Cafeteria diet + C.F. Extract N = 6 | 41.0 ± 4.64 | 0.375 ± 0.061 | 4.28 ± 0.96 |

Values are mean ± SEM

The levels of serum SGPT were increased considerably in cafeteria diet+CF extract treated group as compared to both control untreated and CD group. (Table 4)

TABLE NO. 4

Blood level of serum SGPT, SGOT and ALP: (Liver function tests)

| Groups | SGPT (IU/L) | SGOT (IU/L) | ALP (IU/L) |
|---|---|---|---|
| Control with standard diet N = 6 | 173.3 ± 86.36 | 183 ± 31.76 | 176.7 ± 15.65 |
| CD N = 6 | 58.33 ± 21.64 | 227.5 ± 98.63 | 204 ± 40.07 |
| CD + C.F. Extract N = 6 | 241.2 ± 135.1 | 94.50 ± 45.79 | 71.0 ± 39.60 |

Values are mean ± SEM

The liver and kidney function tests showed no severe toxicity.

(c): Haematological Studies

The hematological parameters were in the normal-range when compared to untreated control and CD group. (Table 5)

TABLE 5

Haematological studies

| Test | Control with Standard diet N = 6 | CD N = 6 | CD + CF Extract N = 6 |
|---|---|---|---|
| Hb gm % | 12.33 ± 0.31 | 13.66 ± 0.34 | 13.98 ± 64.0 |
| WBC/cumm | 7283.33 ± 0.11 | 9833.33 ± 76.8 | 9466 ± 30.2 |
| RBC Million/cumm | 8.27 ± 1.2 | 8.21 ± 34.1 | 8.15 ± 21.3 |
| Platelet count Lac/cumm | 9.26 ± 0.45 | 7.405 ± 9.07 | 8.12 ± 44.1 |
| Neutrophils % | 15.33 ± 0.23 | 13.66 ± 2.32 | 14 ± 0.34 |
| Lymphocytes % | 85.66 ± 32.2 | 79.83 ± 68.0 | 83.5 ± 12.0 |
| HCT % | 48.93 ± 43.6 | 42.78 ± 15.6 | 41.7 ± 40 |
| MCV fl | 60.04 ± 65.5 | 57.43 ± 31.23 | 57.11 ± 12.2 |
| MCH Pg | 15.73 ± 1.24 | 15.35 ± 78.08 | 14.05 ± 0.2 |
| MCHC g/dl | 27.61 ± 14.54 | 26.95 ± 0.21 | 25.83 ± 30 |
| RDW-SD % | 29.15 ± 45.65 | 25.35 ± 54.0 | 24.56 ± 0.6 |
| RDW-CV fl | 16.33 ± 78.0 | 15.1 ± 55.6 | 14.7 ± 0.16 |

Values are mean ± SEM d): Histopathological Studies

The macroscopic and microscopic studies indicated that there was no significant damage to vital organs, which supports the safety of the drug. (Table 5(i)(ii)(iii))

TABLE 5 (i)

Histopathological studies

| Group CD + CF (N = 6) | Heart | Kidney | Spleen | Intestine |
|---|---|---|---|---|
| Microscopy | Epicardium: No Significant pathology Myocardium: No Significant pathology Pericardium: No Significant pathology Valve leaflets: No Significant Pathology No evidence of any pathology | Capsule: No Significant Pathology Glomeruli: Normal cellularity, No significant pathology Tubules: No Significant Pathology Interstitium: Sparse mononuclear cell infiltrate. Vessels: No Significant Pathology | Capsule: No Significant Pathology Red pulp: No Significant pathology White pulp: No Significant pathology Trabeculae: No Significant pathology | Mucosal lining: Unremarkable Lamina propria: Diffuse moderate mononuclear cell Infiltrate. Submncosa: Focal Lymphoid aggregates. Muscularis propria: No significant pathology. Serosa: Scanty diffuse mononuclear cell infiltrate. |
| Impression | Histological findings within normal limits | Histological findings within normal limits | Histological findings within normal limits | Chronic non-specific inflammation. No evidence of malignancy |

TABLE 5 (ii)

| Group CD + CF (N = 6) | Ovaries | Adrenal gland | Liver | Stomach |
|---|---|---|---|---|
| Microscopy | Sections of ovarian tissue show follicles in varying stage of maturation. An occasional corpus luteum is seen. No evidence of malignancy in the sections was observed. | The cortical layers appear unremarkable. The medulla shows no significant pathology. | Lobular architecture appears unremarkable. The hepatocytes are arranged in cords separated by sinusoids. The triads show mild mononuclear cell infiltrate | The lamina propria shows diffuse sparse mononuclear cell infiltrate. The gastric glands appear unremarkable. The muscularis propria shows no significant pathology. |
| Impression | No Significant Pathology. No evidence of malignancy. Histological findings within normal limits | No Significant Pathology. | Mild portal triaditis. | Chronic non-specific inflammation. |

TABLE 5 (iii)

| Groups CD + CF Extract (N = 6) | Brain | Lungs |
|---|---|---|
| Microscopy | No significant pathology | The alveoli appear unremarkable. The intertitium shows sparse mononuclear cell infiltrate and congested capillaries. The bronchioles appear unremarkable. Occasional lymphoid aggregates are noted |
| Impression | No significant Pathology | Chronic Non-specific inflammation |

The CF extract treatment did not cause significant toxicity as revealed by kidney function and liver function tests (refer to tables). The histopathological studies support the safety of the CF extract.

Example 3

Evaluation of Anti-Obesgenic, Glucose Reducing and Cholesterol Reducing Properties of *Caralluma* Extract (C.F.) of the Present Invention in Rats Male Wistar rats (150-200 g) were fed with standard rat diet and specially prepared cafeteria diet (CD) rich in fat. The protocol was approved by the Institutional Animal Ethical Committee before the actual conduct of study.

Three groups of six animals each were formed. Group I was treated as a control group fed with standard diet. Group II was treated with cafeteria diet (CD) and Group III was treated with extract of *Caralluma* fimbriata (CF: 200 mg/kg) along with cafeteria diet with oral gavage for 90 days. All animals were kept under standard laboratory conditions as per the guidelines of CPCSEA.

Body weights of all animals in each group were recorded at the beginning of the study, every week and finally at the end of the study.

At the end of the study blood was collected through retro-orbital plexus and was subjected to biochemical analysis. Dissection of animals was carried out and organs such as liver, spleen, heart, kidney, lungs, stomach, adrenal glands, ovaries and fat pads (epididymis, mensentric) were removed and subjected to histopathological studies.

The results of these studies are provided below.

(a): Evaluation of Body Weights of Rats Fed with Different Diet

TABLE 6(i)

Body weights (gm) of Rats fed with standard diet, CD and CD treated with CF extract of present invention:

|  | Group I: Control with standard diet N = 6 | Group II: CD N = 6 | Group III: CD + C.F tract N = 6 |
|---|---|---|---|
| Initial Weight | 145.0 ± 2.58 | 150 ± 2.58 | 143.3 ± 9.18 |
| 1st week | 152.0 ± 1.03 | 154 ± 5.03 | 149 ± 1.02 |
| 2nd week | 158 ± 7.9 | 157 ± 3.4 | 1158 ± 8.03 |
| 3rd week | 166.09 ± 0.62 | 160 ± 3.6 | 164 ± 5.8 |
| 4th week | 170.5 ± 8.25 | 162.7 ± 10.77 | 170.3 ± 2.29 |
| 5th week | 170.3 ± 2.29 | 1 70.5 ± 8.25 | 162 ± 10.77 |
| 6th week | 1 79.0 ± 2.280 | 174.2 ± 6.32 | 176.7 ± 7.614 |
| 7th week | 178.7 ± 3.69 | 178.5 ± 3.55 | 180.5 ± 8.96 |
| 8th week | 183.5 ± 4.27 | 191.2 ± 4.42 | 186.2 ± 10.3 |
| 9th week | 187.8 ± 3.89 | 205.5 ± 5.75 | 186.5 ± 9.67 |
| 10th week | 181.16 ± 8.51 | 213.16 ± 6.62 | 172.83 ± 3.1 |
| 11th week | 177.83 ± 7.14 | 212.16 ± 5.40 | 165.83 ± 8.37*** |
| 12th week | 185 ± 6.039 | 216.5 ± 6.99 | 169.16 ± 8.5*** |

Values are mean ± SEM,
**$p < 0.01$,
***$p < 0.001$

The results as shown in table 6(i) show that:

The animals in untreated control group show increase in body weight to 127.5% at the end of the study, The animals in the CD group show increase in body weight to 144.0% and The animals in CD+CF extract (Administration of 200 mg/kg CF extract along with CD) group show increase in body weight to 118.0%.

From the results it is concluded that the administration of 200 mg/kg CF extract (caralluma extract prepared in accordance with the present invention) along with CD (cafeteria diet) prevents on increase in body weight caused by the fat rich diet comparison group.

(b): Evaluation of Serum Glucose Levels of Rat Fed with Different Diet

TABLE 6(ii)

Serum glucose levels of rat fed with standard diet, CD and CD treated with CF extract of the present invention

| Groups | Blood Sugar (mg/dl) | Glycosylated Hb (%) |
|---|---|---|
| Control with standard diet N = 6 | 99.67. ± 7.6 | 4.51. ± 0.21 |
| CD N = 6 | 1 14.3: t 1 1.55 | 4.75. ± 0.32 |
| CD + C.F. Extract | 93.00 ± 6.60 | 3.14. ± O.27 |

Values are mean ± SEM

The results as shown in table 6(ii) show that there is a significant rise in blood sugar level in CD group as compared to both control untreated and cafeteria diet+C.F extract treated group (Administration of 200 mg/kg CF extract along with CD). The results show that treatment with a CF extract dose maintains normal glucose levels.

(c): Evaluation of Obesigeniecity Indicators

TABLE 6(iii)

Obesigeniecity indicators

| Groups | Cholesterol (mg/dl) | Triglyceries (mg/dl) | HDL (mg/dl) | LDL (mg/dl) | VLDL (mg/dl) |
|---|---|---|---|---|---|
| Control Untreated N = 6 | 100.16 ± 4.651 | 142.0 ± 13.07 | 29.16 ± 1.86 | 42.61 ± 2.o6 | 28.39 ± 31.76 |
| Cafeteria diet N = 6 | 148.45 ± 18.8 | 132.0 ± 8.96 | 34.66 ± 4.91 | 83.4 ± 20.0 | 3128. ± 98.63 |
| Cafeteria diet + C.F. Extract N = 6 | 96.88 ± 5.285** | 83.67 ± 11.37 | 30.13 ± 2.58 | 51.01 ± 6.78 | 15.73 ± 1.69 |

Values are mean ± SEM,
**$p < 0.01$ Interpretation

The results as shown in table 6(iii) show that:
Feeding of cafeteria diet produces a significant increase in total serum cholesterol and LDL levels in CD group.
Cafeteria diet+C.F extract treated group shows significant decrease in level of cholesterol and triglycerides The results provided in Table 6 (iii) also show that the administration of 200 mg/kg CF extract (caralluma extract prepared in accordance with the present invention) along with CD (cafeteria diet) prevents the increase in the level of obesegenicity indicators.

The evaluation of anti-obesigenic property of CF extract in diet induced obese rat model reveals that concurrent administration of CF extract with cafeteria diet prevents the rats from becoming obese. The increasing levels of obesity parameters such as total cholesterol, triglycerides, LDL and VLDL were controlled by the administration of CF extract. The results from the anti-obesigenic study show that CF extract at the dose of 200 mg/kg body weight administered with cafeteria diet significantly reduces the body weight and obesity parameters.

Example 4

A 39 year old female patient presented with obesity. Prior to the instruction of treatment of the treatment her weight was 88 kg. She was treated with a formulation prepared in accordance with the present invention at a dose of 500 mg twice a day before meals for a period of 60 days without any concomitant administration of other anti-obesity drugs. After 60 days her weight had decreased by 10%.

Example 5

Comparison of Prior Art Formulation to Invention

The comparative analysis of an existing caralluma marketed product and the *Caralluma* extract of the present invention has been done based on the following study in rats:

(a) Body weights of rats fed with extract of prior art and that of invention
(b) Serum glucose levels of rat fed extract of prior art and that of invention
(c) Obesigeniecity indicators All the aforesaid comparisons have been discussed as examples mentioned below:

(a) Comparison of Body Weight of Rats Fed with the Extract Described in the Prior Art and that of Present Invention

TABLE 7

Prior art
Body weight of rats fed cafeteria diet, with or without Caralluma extract(CFE)

| GROUPS | Initial Weight | 1st week | 2nd week | 3rd week | 4th week | 5th week | 6th week |
|---|---|---|---|---|---|---|---|
| Untreated control (N = 6) | 201.67 ± 1.16 | 208.33 ± 2.40 | 220.00 ± 3.22 | 232.06 ± 2.02 | 238.66 ± 3.16 | 242.66 ± 3.23 | 248.12 ± 3.12 |
| Cafeteria (CA) (N = 6) | 203.33 ± 154 | 228.33 ± 1.40 | 245.00 ± 4.21 | 255.02 ± 4.55 | 273.33 ± 3.12 | 284.32 ± 3.12 | 299.56 ± 3.56 |
| CA + 5 mg of 25% CFE (N = 6) | 219.10 ± 2.00 | 225.66 ± 2.52 | 232.23 ± 2.81 | 238.33 ± 2.54 | 246.66 ± 3.09 | 255.10 ± 2.79 | 264.44 ± 3.56 |
| CA + 10 mg of 25% CFE (N = 6) | 213.32 ± 2.33 | 220.23 ± 3.23 | 227.34 ± 3.23 | 232.43 ± 3.32 | 238.35 ± 3.44 | 244.53 ± 3.31 | 249.56 ± 2.55 |

TABLE 7-continued

Prior art
Body weight of rats fed cafeteria diet, with or without Caralluma extract(CFE)

| | | | | | | | |
|---|---|---|---|---|---|---|---|
| CA + 20 mg of 25% CFE (N = 6) | 212.12 ± 2.23 | 218.87 ± 2.68 | 223.78 ± 2.32 | 228.99 ± 2.38 | 234.86 ± 3.22 | 239.98 ± 2.34 | 245.86 ± 3.12 |

| GROUPS | 7th week | 8th week | 9th week | 10th week | 11th week | 12th week |
|---|---|---|---|---|---|---|
| Untreated control (N = 6) | 258.87 ± 3.90 | 267.90 ± 4.30 | 275.89 ± 3.78 | 284.12 ± 2.67 | 290.67 ± 3.90 | 29766 ± 278 |
| Cafeteria (CA) (N = 6) | 309.45 ± 4.34 | 317.43 ± 3.23 | 329.67 ± 4.42 | 338.45 ± 3.56 | 346.78 ± 2.44 | 350.34 ± 2.13 |
| CA + 5 mg of 25% CFE (N = 6) | 271.56 ± 3.45 | 277.57 ± 3.67 | 284.87 ± 3.33 | 293.76 ± 3.12 | 302.87 ± 3.33 | 312.12 ± 3.21 |
| CA + 10 mg of 25% CFE (N = 6) | 257.56 ± 3.42 | 264.77 ± 3.68 | 271.78 ± 3.13 | 278.77 ± 3.58 | 285.78 ± 2.65 | 291.25 ± 3.11 |
| CA + 20 mg of 25% CFE (N = 6) | 252.98 ± 2.90 | 259.98 ± 3.80 | 266.89 ± 3.23 | 271.90 ± 1.23 | 279.98 ± 2.12 | 288.50 ± 2.11 |

Values are mean ± SEM; a, $p < 0.05$ between untreated control and cafeteria diet-fed; b, $p < 0.05$ between cafeteria diet-fed and cafeteria diet + CFE-fed The table 7 indicates that:
The animals in untreated control group shows increase in weight to 147.50% at the end of experiment.
Those in the CA group shows increase in weight to 172.30%.
Those in Ca+20 mg CFE group shows increase in weight to 136%.

In case of the present invention, initial weight of rat was 143.3. The weight of rats during the 12th week, when rats were fed with the extract of the present invention i.e. CD+C.F extract (Administration of 200 mg/kg CF along with CD-Cafeteria diet) was 169.16. (Table 8)

TABLE 8

Present Invention
Body weights (gin) of Rats fed with standard diet, CD and CD treated with CF extract:

| Groups | Initial Weight | 1st week | 2nd week | 3rd week | 4th week | 5th week | 6th week |
|---|---|---|---|---|---|---|---|
| Control with standard diet N = 6 | 145.0 ± 2.58 | 152.0 ± 1.03 | 158 ± 7.9 | 166.09 ± 0.62 | 170.5 ± 8.25 | 170.3 ± 2.29 | 179.0 ± 2.280 |
| CD (N = 6) | 150 ± 2.58 | 154 ± 5.03 | 157 ± 3.4 | 160 ± 3.6 | 162.7 ± 10.77 | 170.5 ± 8.25 | 174.2 ± 6.32 |
| CD + C.F extract N = 6 | 143.3 ± 9.18 | 149 ± 1.02 | 158 ± 8.03 | 164 ± 5.8 | 170.3 ± 2.29 | 162 ± 10.77 | 176.7 ± 7.614 |

| Groups | 7th week | 8th week | 9th week | 10th week | 11th week | 12th week |
|---|---|---|---|---|---|---|
| Control with standard diet N = 6 | 178.5 ± 3.55 | 183.5 ± 4.27 | 187.8 ± 3.89 | 181.16 ± 8.51 | 177.83 ± 7.14 | 185 ± 6.039 |
| CD (N = 6) | 178.7 ± 3.69 | 191.2 ± 4.42 | 205.5 ± 5.75 | 213.16 ± 6.62 | 212.16 ± 5.40 | 216.5 ± 6.99 |
| CD + C.F extract N = 6 | 180.5 ± 8.96 | 186.2 ± 10.3 | 186.5 ± 9.67 | 172.83 ± 3.1" | 165.83 ± 8.37*** | 169.16 ± 8.5*** |

Values are mean ± SEM,
**$P < 0.01$,
***$P < 0.001$

The table 8 indicates that:

The animals in untreated control group shows increase in weight to 127.5% at the end of experiment.
Those in the CA group shows increase in weight to 144.0%.
Those in Ca+20 mg CFE group shows increase in weight to 118.0%.

From the results as shown in table 7 and 8 it is clear that:
In the case of the prior art, the initial weight of the rat was 212.12. The weight during the 12th week, when rats were fed with extract from the prior art (CA (Cafeteria diet)+20 mg of 25% CFE) increased to 288.5. (Table 7)

The increase in body weight to 136.01% in case of prior art whereas in case of present invention, the animals in CD+CF extract group show increase in body weight to 118.0%.

This direct comparison shows that the increase in the body weight of rats administered formulations according to the present invention was much less than the body weight of rats administered formulations according to the prior art.

(b) Comparison of Serum Glucose Levels of Rats Fed with the Extract of Prior Art and Present Invention

TABLE 9

Prior Art
Serum glucose levels of rat fed with *Caralluma* extract (CFE)

| Group | Blood sugar (mg/dL) | % difference |
|---|---|---|
| Untreated control (N = 6) | 95.83 ± 0.82 | |
| Cafeteria (CA) (N = 6) | 189.88 ± O.93 | 198.14% |
| CA + 5 mg of 25% CFE (N = 6) | 163.08 ± 0.58 | 170.17% |
| CA + 10 mg of 25% CFE (N = 6) | 143.93 ± 0.71 | 150.19% |
| CA + 20 mg of 25% CFE (N = 6) | 118.01 ± 0.28 | 123.14% |

TABLE 10

Present Invention
Serum glucose levels of rat fed with standard diet, CD and CD treated with *caralluma* extract (CF extract)

| Groups | Blood Sugar (mg/dL) |
|---|---|
| Control with standard diet N = 6 | 99.67. ± 7.6 |
| CD N = 6 | 1 14.3: t 1 1.55 |
| CD + C.F. Extract | 93.00 ± 6.60 |

Values are mean ± SEM

The results provided in Tables 9 and 10 show that:
In case of the prior art, the blood sugar level of untreated rats was 95.83 mg/dL. The rats fed with *Caralluma* extract (CA+20 mg of 25% CFE) had the blood sugar level of 118.01 rag/dL. (Table 9)
In case of present invention, the blood sugar level of untreated rats was 99.67 ing/dL. The rats fed with *Caralluma* extract i.e. CD+C.F. Extract (Administration of 200 mg/kg CF extract along with CD) had blood sugar level of 93.00 mg/dL. (Table 10)
In case of prior art the increase in serum glucose level in rats is to 12114%
In case of the present invention the decrease in serum glucose level in rats is to 93.31%

This comparison shows that the increase in serum glucose levels of rats administered formulations according to the present invention much lower than the levels for rats administered prior art formulations.

(c) Comparison of Obesigeniecity Indicators for Extract of Prior Art and that of Present Invention

TABLE 11

Prior Art
Obesigeniecity indicators for extract of the prior art

| Group | Cholestrol (mg/dL) | % difference | Triglyceride (mg/dL) | % difference |
|---|---|---|---|---|
| Untreated control (N = 6) | 74.78 ± 0.46 | | 72.59 ± 0.97 | |
| Cafeteria (CA) (N = 6) | 94.15 ± 0.48 | 125.90% | 150.82 ± 1.61 | 207.76% |
| CA + 5 mg of 25% CFE (N = 6) | 89.19 ± 1.61 | 119.26% | 117.30 ± 0.92 | 161.59% |
| CA + 10 mg of 25% CFE (N = 6) | 82.85 ± 1.72 | 110.79% | 108.37 ± 1.51 | 149.29% |
| CA + 20 mg of 25% CFE (N = 6) | 76.29 ± 1.28 | 102.01% | 95.88 ± 0.75 | 132.08% |

TABLE 12

Present Invention
Obesigeniecity indicators for the present invention

| Groups | Cholesterol (mg/dl) | Triglyceries (mg/dl) |
|---|---|---|
| Control Untreated N = 6 | 100.16 ± 4.651 | 142.0 ± 13.07 |
| Cafeteria diet N = 6 | 148.45 ± 18.8 | 132.0 ± 8.96 |
| Cafeteria diet + C.F. Extract N = 6 | 96.88 ± 5.285** | 83.67 ± 11.37 |

Values are mean ± SEM,
**p < 0.01 Interpretation

The results provided in Tables 11 and 12 show that:
In case of the prior art, the cholesterol level for untreated rats is 74.78 mg/dL and for rats fed with *Caralluma* extract (CA+20 mg of 25% CFE) is 76.29 mg/dL.
In case of the prior art, the level of triglyceride for untreated rats is 72.59 mg/dL and for rats fed with *Caralluma* extract (CA+20 mg of 25% CFE) is 95.88 mg/dL
In case of the present invention, the cholesterol level for untreated rats is 100.16 mg/dL and for the rats fed with *Caralluma* extract i.e. CD+C.F. Extract (Administration of 200 mg/kg CF extract along with CD) is 96.88 mg/dL
In case of the present invention, the level of triglyceride for untreated rats is 142.0 mg/dL for the rats fed with *Caralluma* extract i.e. CD+C.F. Extract (Administration of 200 mg/kg CF extract along with CD) is 83.67 mg/dL
In case of the prior art the increase in cholesterol level in rats is 102.01%
In case of the present invention decrease in cholesterol level in rats is 96.72%
In case of the prior art the increase in triglyceride level in rats is 132.08%
In case of the present invention decrease in triglyceride level in rats is 75.59%

This comparison shows that the extract prepared in accordance with the present invention has significantly higher cholesterol and triglyceride reducing activity as compared to prior art extract.

As described herein the processes for preparing the *Caralluma* extract in accordance with the present invention provide, several advantages including:
a) The processes do not employ carcinogenic solvents such as hexane to remove resinous material from the extract.
b) The step of drying of the *Caralluma* extract does not use drying additives such as Malto-Dextrin or magnesium carbonate.

c) The processes provide highly pure products.

d) The processes are economic and less time-consuming.

Furthermore extracts prepared according to the present invention have significantly enhanced anti-obesigenic, glucose level reducing and cholesterol level reducing activities.

While considerable emphasis has been placed herein on the various components of preferred embodiments of the invention, it will be appreciated that alterations and modifications can be made in preferred embodiments without departing from the principles of the invention. These and other changes in the preferred embodiment as well as other embodiments of the invention will be apparent to those skilled in the art from the disclosure herein, whereby it is to be distinctly understood that the foregoing descriptive matter is to be interpreted merely as illustrative of the invention and not as a limitation.

What is claimed is:

1. A method for preparing a *Caralluma* extract, comprising the steps of:
   a. drying a *Caralluma* plant material;
   b. treating the dried *Caralluma* plant material by at least one operation selected from a group consisting of sorting, cleaning and sizing and any combination thereof to obtain *Caralluma* plant material for extraction;
   c. iteratively extracting the *Caralluma* plant material with a first ethanol containing solvent system for at least two initial iterations followed by at least two subsequent iterations with a second ethanol containing solvent system to obtain a diluted extract, wherein the concentration of ethanol in the first and second solvent system is 80% and 50% with respect to the volume of each solvent system respectively;
   d. removing the solvent from the diluted extract by distillation at a temperature below about 40° C. to obtain a concentrate;
   e. chilling the concentrate at a temperature between about 6 to about 10° C. for a period of between about 7 to about 8 hours to obtain a chilled concentrate;
   f. filtering the chilled concentrate to obtain a filtrate;
   g. concentrating the filtrate at a temperature below about 60° C. to obtain a viscous liquid;
   h. spray drying the concentrated viscous liquid to obtain a powder; and
   i. pulverizing and sifting the dried powder to obtain a *Caralluma* extract.

2. The method of claim 1, wherein the *Caralluma* plant material is obtained from a group of *Caralluma* species selected from the group consisting of: *Caralluma burchardii, Caralluma acutangula, Caralluma adscendens, Caralluma edulis, Caralluma fimbriata, Caralluma negevensis, Caralluma somalica, Caralluma speciosa* and any combination thereof.

3. The method of claim 1, wherein the *Caralluma* plant material comprises *Caralluma fimbriata*.

4. The method of claim 1, wherein the first and the second ethanol containing solvent systems comprise a solvent selected from the group consisting of: water, methanol, isopropyl alcohol, n-butanol and hydro alcohol and any combination thereof.

5. The method of claim 1, wherein concentrating in method step g is carried out at a temperature in a range of about 55 to about 60° C.

* * * * *